US010249173B1

(12) United States Patent
Braun et al.

(10) Patent No.: US 10,249,173 B1
(45) Date of Patent: *Apr. 2, 2019

(54) MONITORING SYSTEMS AND METHODS FOR PERSONAL SAFETY

(71) Applicant: United Services Automobile Association, San Antonio, TX (US)

(72) Inventors: Florian Braun, San Antonio, TX (US); Andre Rene Buentello, San Antonio, TX (US); Jess W. Gingrich, San Antonio, TX (US); Timothy Altman, Bulverde, TX (US); Terry Benton, Celina, TX (US)

(73) Assignee: United Services Automobile Association, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/000,314

(22) Filed: Jun. 5, 2018

Related U.S. Application Data

(63) Continuation of application No. 15/253,242, filed on Aug. 31, 2016, now Pat. No. 10,013,871.

(60) Provisional application No. 62/214,022, filed on Sep. 3, 2015.

(51) Int. Cl.
G08B 25/01 (2006.01)
G08B 25/10 (2006.01)
G08B 27/00 (2006.01)

(52) U.S. Cl.
CPC .......... G08B 25/016 (2013.01); G08B 25/10 (2013.01); G08B 27/00 (2013.01)

(58) Field of Classification Search
CPC ....... G08B 25/016; G08B 25/10; G08B 27/00
USPC .......................... 340/539.1, 539.11, 539.13
See application file for complete search history.

(56) References Cited

U.S. PATENT DOCUMENTS

| | | | |
|---|---|---|---|
| 5,959,529 A | 9/1999 | Kail, IV | |
| 6,084,510 A | 7/2000 | Lemelson et al. | |
| 9,171,450 B2 | 10/2015 | Cho et al. | |
| 10,013,871 B1 * | 7/2018 | Braun | G08B 25/016 |
| 2010/0226210 A1 | 9/2010 | Kordis et al. | |
| 2010/0228482 A1 | 9/2010 | Yonak | |
| 2012/0026836 A1 | 2/2012 | Scripca et al. | |

* cited by examiner

Primary Examiner — Daryl C Pope
(74) Attorney, Agent, or Firm — Locke Lord LLP; Christopher J. Capelli

(57) ABSTRACT

A computer-implemented method for monitoring a condition of a person includes receiving, at a computerized device, at least one signal from a condition sensor and determining if a condition is an emergency condition of a user based on the at least one signal.

20 Claims, 4 Drawing Sheets

MONITORING SYSTEMS AND METHODS FOR PERSONAL SAFETY

CROSS REFERENCE TO RELATED APPLICATIONS

This application is a Continuation of U.S. patent application Ser. No. 15/253,242,036 filed Aug. 31, 2016, which claims priority to U.S. Patent Application Ser. No. 62/214,022 filed Sep. 3, 2015 which is incorporated herein by reference in its entirety.

FIELD OF THE DISCLOSURE

The disclosed embodiments generally relates to monitoring systems, more specifically to monitoring systems for personal safety.

BACKGROUND

Traditional monitoring systems require manual initiation by a user in order to send an emergency signal to a monitoring body (e.g., police, a subscription monitoring service). However, certain emergency circumstances do not allow for a user to manually indicate an emergency condition (e.g., in a surprise assault). Also, traditional systems are limited to indication of an emergency condition that notifies the monitoring body. Improvements to monitoring systems would be beneficial.

SUMMARY

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings. To achieve these and other advantages and in accordance with the purpose of the illustrated embodiments, in one aspect, a computer-implemented method for monitoring a condition of a person includes receiving, at a computerized device, at least one signal from a condition sensor and determining if a condition is an emergency condition of a user based on the at least one signal.

The condition sensor can be a sonic device configured to ping surroundings to indicate at least one of location, velocity, or acceleration of at least one object relative to the user within a predetermined area. The at least one object can include at least one of people, vehicles, or animals.

The condition can be determined to be an emergency condition if the location of the at least one object is within a predetermined personal space of the user. The computerized device can be a mobile phone. The method can further include transmitting a signal to a monitoring body if an emergency condition is determined.

The method can further include notifying the user if an emergency condition is determined. Notifying the user can include activating a tactile, auditory, and/or other alarm to indicate an emergency condition to the user for the user to take emergency action.

The method can further include transmitting an emergency signal to one or more non-user electronic devices within a monitoring network to notify the non-user electronic devices of an emergency condition.

The one or more non-user electronic devices can include at least one of a camera, a mobile device of another person or officer in the vicinity, and/or an automated device configured to locate, follow, or otherwise monitor the user in the emergency condition.

In accordance with at least one aspect of this disclosure, a system can include a network of electronic devices configured to receive an emergency signal from a user and a response module executed by each electronic device to cause each electronic device to take an emergency action when the emergency signal is received.

In certain embodiments, the electronic devices include a camera. The response module can cause the camera to point in a direction of the user when the emergency signal is received. In certain embodiments, the electronic devices include drone aircraft.

An electronic device includes a memory, a processor operatively connected to the memory, and a response module stored on the memory and configured to receive and emergency signal and cause the electronic device to take an emergency action from a user device when the emergency signal is received.

The emergency signal can include user device data. The user device data can include user device location. The electronic device can include a camera configured to turn on and/or point in a direction of the user device based on the user device data. In certain embodiments, the electronic device can include one or more drone aircraft for locating, following, and/or monitoring a user based on the user device data.

BRIEF DESCRIPTION OF THE DRAWINGS

The accompanying appendices and/or drawings illustrate various non-limiting, example, aspects in accordance with the present disclosure.

DETAILED DESCRIPTION OF CERTAIN EMBODIMENTS

Figure 1:
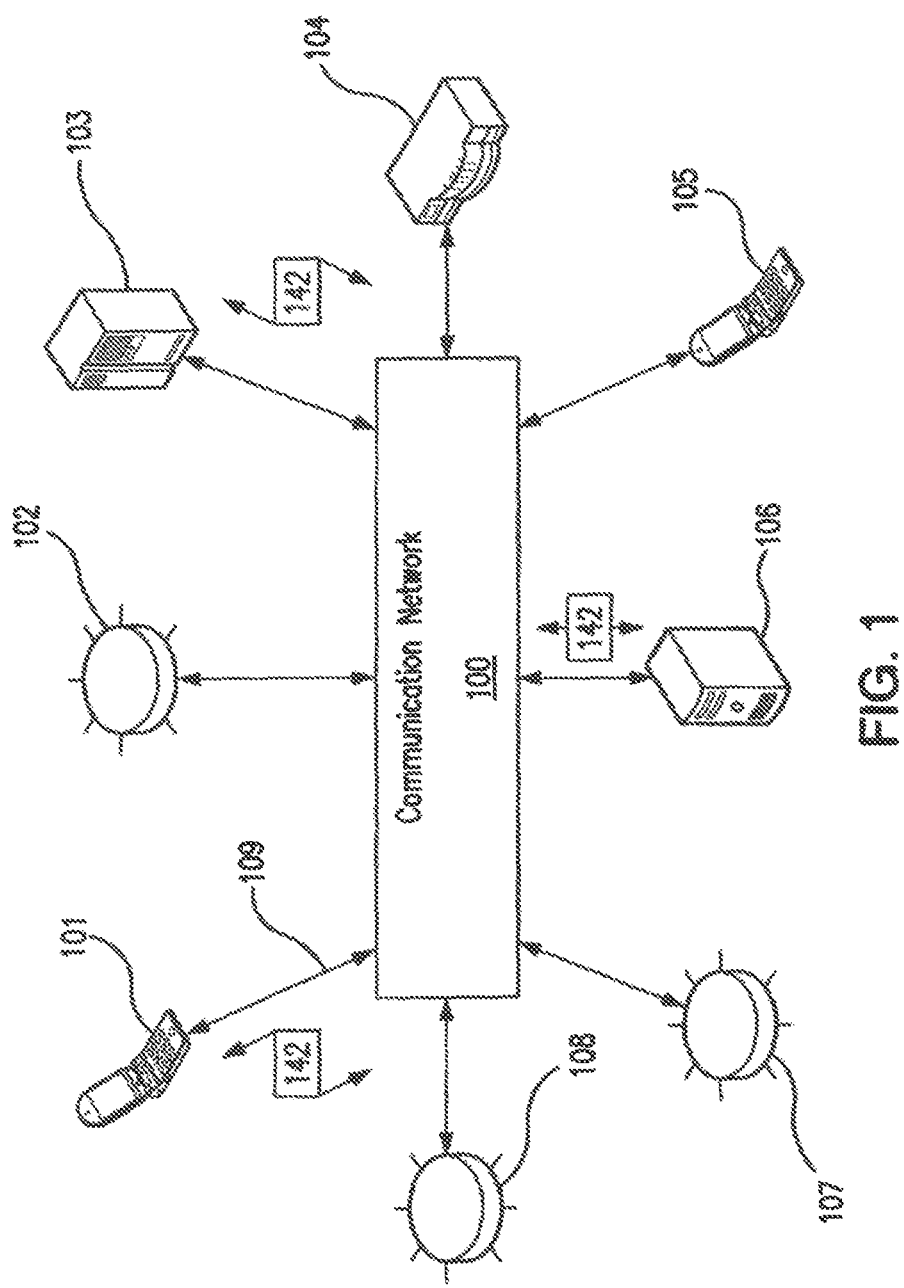
FIG. 1 illustrates an example communication network in accordance with this disclosure.

The illustrated embodiments are now described more fully with reference to the accompanying drawings wherein like reference numerals identify similar structural/functional features. The illustrated embodiments are not limited in any way to what is illustrated as the illustrated embodiments described below are merely exemplary, which can be embodied in various forms, as appreciated by one skilled in the art. Therefore, it is to be understood that any structural and functional details disclosed herein are not to be interpreted as limiting, but merely as a basis for the claims and as a representation for teaching one skilled in the art to variously employ the discussed embodiments. Furthermore, the terms and phrases used herein are not intended to be limiting but rather to provide an understandable description of the illustrated embodiments.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the illustrated embodiments, exemplary methods and materials are now described.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the illustrated embodiments discussed below can be a software algorithm, program or code residing on computer useable medium having control logic for enabling execution on a machine having a computer processor. The machine typically includes memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine. The embodiments described herein include such software to implement the equations, relationships and algorithms described above. One skilled in the art will appreciate further features and advantages of the illustrated embodiments based on the above-described embodiments. Accordingly, the illustrated embodiments are not to be limited by what has been particularly shown and described, except as indicated by the appended claims.

Turning now descriptively to the drawings, in which similar reference characters denote similar elements throughout the several views, FIG. 1 depicts an exemplary communications network 100 in which below illustrated embodiments may be implemented.

It is to be understood a communication network 100 can be a geographically distributed collection of nodes interconnected by communication links and segments for transporting data between end nodes, such as personal computers, work stations, smart phone devices, tablets, televisions, sensors and or other devices such as automobiles, etc. Many types of networks are available, with the types ranging from local area networks (LANs) to wide area networks (WANs). LANs typically connect the nodes over dedicated private communications links located in the same general physical location, such as a building or campus. WANs, on the other hand, typically connect geographically dispersed nodes over long-distance communications links, such as common carrier telephone lines, optical lightpaths, synchronous optical networks (SONET), synchronous digital hierarchy (SDH) links, or Powerline Communications (PLC), and others.

FIG. 1 is a schematic block diagram of an example communication network 100 illustratively comprising nodes/devices 101-108 (e.g., sensors 102, client computing devices 103, smart phone devices 105, web servers 106, routers 107, switches 108, and the like) interconnected by various methods of communication. For instance, the links 109 may be wired links or may comprise a wireless communication medium, where certain nodes are in communication with other nodes, e.g., based on distance, signal strength, current operational status, location, etc. Moreover, each of the devices can communicate data packets (or frames) 142 with other devices using predefined network communication protocols as will be appreciated by those skilled in the art, such as various wired protocols and wireless protocols etc., where appropriate. In this context, a protocol consists of a set of rules defining how the nodes interact with each other. Those skilled in the art will understand that any number of nodes, devices, links, etc. may be used in the computer network, and that the view shown herein is for simplicity. Also, while the embodiments are shown herein with reference to a general network cloud, the description herein is not so limited, and may be applied to networks that are hardwired.

As will be appreciated by one skilled in the art, aspects of this disclosure may be embodied as a system, method or computer program product. Accordingly, aspects of this disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure are described below with reference to flowchart illustrations and/or block diagrams of methods, apparatus (systems) and computer program products according to embodiments of disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 2:
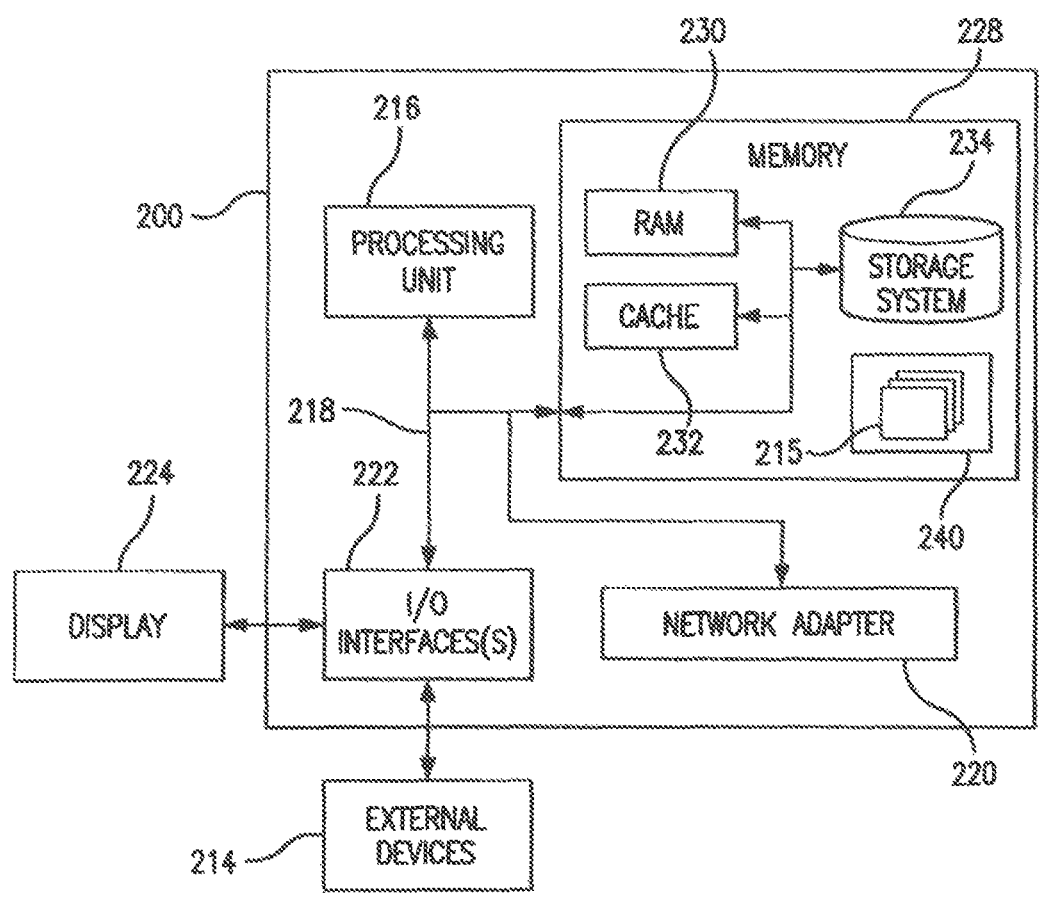
FIG. 2 illustrates an example network device/node in accordance with this disclosure.

FIG. 2 is a schematic block diagram of an example network computing device 200 (e.g., client computing device 103, server 106, etc.) that may be used (or components thereof) with one or more embodiments described herein, e.g., as one of the nodes shown in the network 100. As explained above, in different embodiments these various devices are configured to communicate with each other in any suitable way, such as, for example, via communication network 100.

Device 200 is intended to represent any type of computer system capable of carrying out the teachings of various embodiments of this disclosure. Device 200 is only one example of a suitable system and is not intended to suggest any limitation as to the scope of use or functionality of embodiments of disclosure described herein. Regardless, computing device 200 is capable of being implemented and/or performing any of the functionality set forth herein.

Computing device 200 is operational with numerous other general purpose or special purpose computing system environments or configurations. Examples of well-known computing systems, environments, and/or configurations that may be suitable for use with computing device 200 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, and distributed data processing environments that include any of the above systems or devices, and the like.

Computing device 200 may be described in the general context of computer system-executable instructions, such as program modules, being executed by a computer system. Generally, program modules may include routines, programs, objects, components, logic, data structures, and so on that perform particular tasks or implement particular abstract data types. Computing device 200 may be practiced in distributed data processing environments where tasks are performed by remote processing devices that are linked through a communications network. In a distributed data processing environment, program modules may be located in both local and remote computer system storage media including memory storage devices.

Device 200 is shown in FIG. 2 in the form of a general-purpose computing device. The components of device 200 may include, but are not limited to, one or more processors or processing units 216, a system memory 228, and a bus 218 that couples various system components including system memory 228 to processor 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing device 200 typically includes a variety of computer system readable media. Such media may be any available media that is accessible by device 200, and it includes both volatile and non-volatile media, removable and non-removable media.

System memory 228 can include computer system readable media in the form of volatile memory, such as random access memory (RAM) 230 and/or cache memory 232. Computing device 200 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of disclosure.

Program/utility 240, having a set (at least one) of program modules 215, such as underwriting module, may be stored in memory 228 by way of example, and not limitation, as well as an operating system, one or more application programs, other program modules, and program data. Each of the operating system, one or more application programs, other program modules, and program data or some combination thereof, may include an implementation of a networking environment. Program modules 215 generally carry out the functions and/or methodologies of embodiments of disclosure as described herein.

Device 200 may also communicate with one or more external devices 214 such as a keyboard, a pointing device, a display 224, etc.; one or more devices that enable a user to interact with computing device 200; and/or any devices (e.g., network card, modem, etc.) that enable computing device 200 to communicate with one or more other computing devices. Such communication can occur via Input/Output (I/O) interfaces 222. Still yet, device 200 can communicate with one or more networks such as a local area network (LAN), a general wide area network (WAN), and/or a public network (e.g., the Internet) via network adapter 220. As depicted, network adapter 220 communicates with the other components of computing device 200 via bus 218. It should be understood that although not shown, other hardware and/or software components could be used in conjunction with device 200. Examples, include, but are not limited to: microcode, device drivers, redundant processing units, external disk drive arrays, RAID systems, tape drives, and data archival storage systems, etc.

FIGS. 1 and 2 are intended to provide a brief, general description of an illustrative and/or suitable exemplary environment in which embodiments of this disclosure may be implemented. FIGS. 1 and 2 are exemplary of a suitable environment and are not intended to suggest any limitation as to the structure, scope of use, or functionality of an embodiment of this disclosure. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

Figure 3:
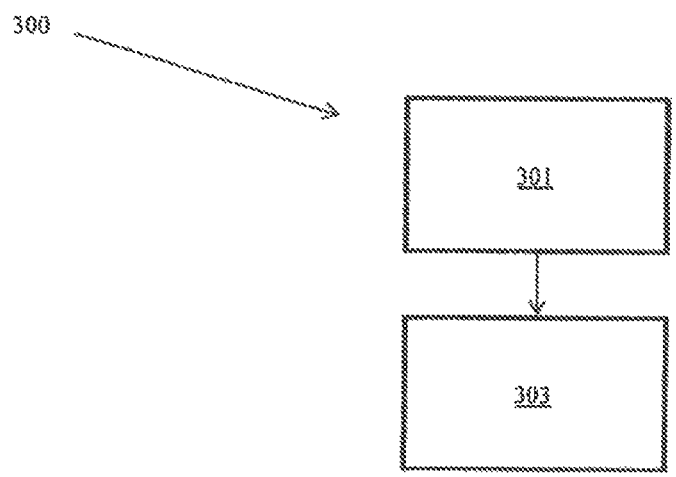
FIG. 3 illustrates an embodiment of a method in accordance with this disclosure.

With the exemplary communication network 100 (FIG. 1) and computing device 200 (FIG. 2) being generally shown and discussed above, description of certain illustrated embodiments of this disclosure will now be provided. With reference now to FIG. 3, shown is a flow chart demonstrating implementation of the various exemplary embodiments. It is noted that the order of steps shown in FIG. 3 is not required, so in principle, the various steps may be performed out of the illustrated order. Also certain steps may be skipped, different steps may be added or substituted, or selected steps or groups of steps may be performed in a separate application following the embodiments described herein.

In accordance with this disclosure, referring to FIG. 3, a computer-implemented method 300 for monitoring a condition of a person includes receiving, at a computerized device (e.g., a device 200 as described above), at least one signal from a condition sensor (e.g., at block 301). The method 300 also includes determining, e.g., at block 303, if a condition is an emergency condition of a user based on the at least one signal. For example, the device 200 can include an emergency module stored on the memory thereof and configured to determine if an emergency condition exists. However, it is contemplated that the emergency module can be stored on any other suitable device in communication with the condition sensor and/or device 200.

Figure 4:
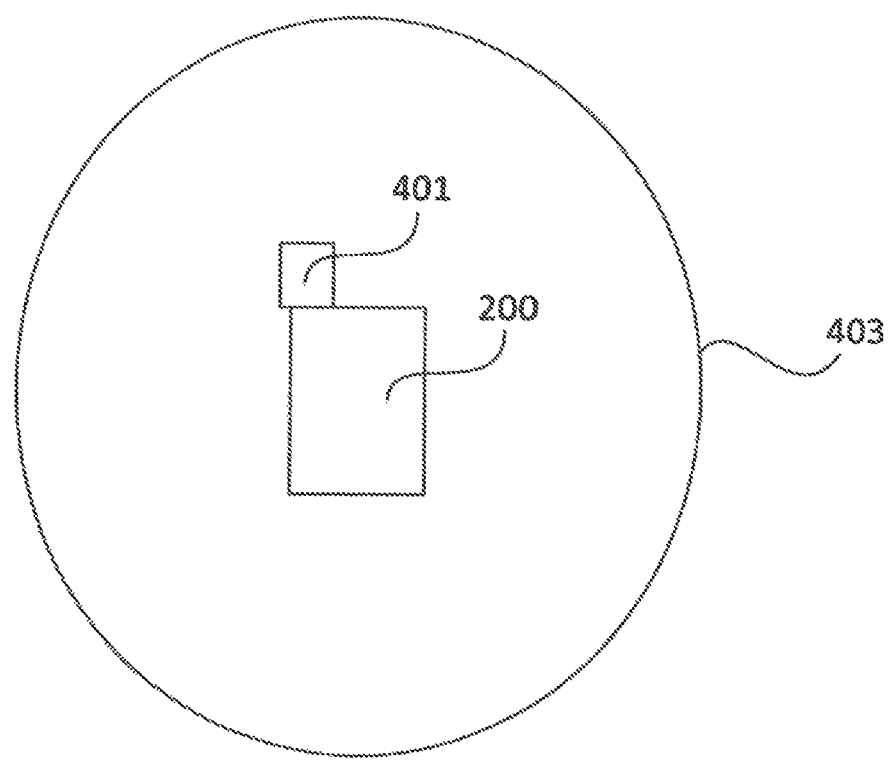
FIG. 4 illustrate an embodiment of a device and condition sensor in accordance with this disclosure.

Referring additionally to FIG. 4, in certain embodiments, the condition sensor can be a sonic device 401 configured to ping surroundings to indicate at least one of location, velocity, and/or acceleration of at least one object relative to the user within a predetermined area 403. For example, the sonic device 401 can operatively connect to the computerized device 200 (e.g., at a data port of a mobile phone, via Bluetooth, or any other suitable manner). The sonic sensor 401 can be configured to detect any suitable objects (e.g., people, vehicles, and/or animals). The condition can be determined to be an emergency condition if the location of the at least one object is within the predetermined area 403 (e.g., a predetermined personal space of the user). It is contemplated that the predetermined area 403 can be modified and/or otherwise defined by the user (e.g., to have further distance in a blind spot direction, to have a wider area).

Additionally or alternatively, an emergency condition can be determined if any other quality of the object is determined to be above a certain threshold. For example, if an object has a velocity and/or acceleration above a certain threshold such that the object will enter the predetermined area 403, then an emergency condition can be determined to exist.

It is contemplated that any other suitable condition sensors (e.g., a thermal sensor) or combination thereof can be similarly connected to the user's device 200 and/or used in addition to or alternative of a sonic device. Also, any suitable condition sensor can be used to sense any suitable condition (e.g., an approaching object as described above, a location of the user, whether the user has fallen over). For example, the condition sensor can indicate a fall condition such that if a user falls to the ground, the emergency condition can be determined. It is contemplated that the user's device can collect information on near-by wifi and/or Bluetooth signals to enhance location ability in addition to the condition sensor and/or other inboard locations devices (e.g., GPS).

In certain embodiments, the condition sensor can be at least partially embodied in a condition module stored on the memory of the device 200. For example, the condition module can be operatively connected to a mapping module (e.g., operatively connected to a GPS of device 200) to determine if a user is within predetermined limits of a predetermined route. For example, if a user is out running, they can program a predetermined safety route into the mapping module. If the user is determined to be off route by a predetermined distance, an emergency condition can be determined.

In one illustrated embodiment, the device 200 is configured to store a predetermined route to be followed by a user (e.g., a jog path route), with the device 200 further being configured to store the estimated time it will take for the user to traverse the aforesaid route (e.g., jogging time). The device 200 may further be configured to store an average rate of estimated travel speed while the aforesaid route is traversed by the user. Upon initiation of route travel by a user, device 200 is configured to not only track the predetermined route, but also determine deviations therefrom, including but not limited to, route deviation, speed deviation and/or time deviation. For instance, if a user deviates from the route a predetermined distance, or the travel speed and/or time required to travel the route deviates a predetermined threshold (which may be user prescribed), the device 200 is configured to trigger an alarm/alert condition (e.g., an attack, fall or route deviation). As discussed below, this may include transmitting an alert signal to a monitoring organization and/or providing an audio and/or visual alarm signal from the device to indicate the determined emergency situation as well as to deter a possible assailant.

The method 300 can further include transmitting a signal to a monitoring organization (e.g., the authorities, a safety service, a known contact, etc.) if an emergency condition is determined. For example, the emergency module can send a signal to the police (e.g., a police officer in vicinity) with user device data (e.g., that indicates user location or other device information) if an emergency condition is determined.

In certain embodiments, the user's device 200 can be configured to automatically and/or continuously send data regarding the condition of the user from the condition sensor and/or other portions of device 200 to one or more remote servers (e.g., the cloud) for storage and use (e.g., to locate the user, to provide evidence). For example, in an emergency condition, the device 200 can automatically push condition data to the cloud and allow access to the appropriate personnel. This can be done when transmitting a signal to the monitoring body or at any other suitable time (e.g., before, after, or continuously irrespective of an emergency condition).

The method can further include notifying the user if an emergency condition is determined (either when determined or imminent). Notifying the user can include activating a tactile, auditory, and/or other alarm to indicate an emergency condition to the user for the user to take emergency action. For example, a user may have earbuds or other headphones that are connected to device 200 which allow the user to be notified of a particular object (e.g., with an automated voice indicating which direction the object is coming from and/or any other suitable sound).

In certain embodiments, the method can further include transmitting an emergency signal to one or more non-user electronic devices within a monitoring network to notify the non-user electronic devices of an emergency condition. For example, the emergency module can be configured to send a signal to a suitable device (e.g., as described above) that is configured to receive such a signal. In certain embodiments, the network of devices can include at least one of a camera, a mobile device of another person or officer in the vicinity, and/or an automated device (e.g., a drone aircraft) configured to locate, follow, or otherwise monitor the user in the emergency condition.

The non-user electronic devices can include a response module stored on a memory thereof and executed by each electronic device to cause each electronic device to take an emergency action when the emergency signal is received. For example, in embodiments including at least one camera, the response module can cause the camera to turn on and/or point in a direction of the user when the emergency signal is received in order to take video, audio, and/or pictures of the emergency condition. In this respect, any event the user is experiencing can be monitored by any suitable camera in the vicinity. For example, the user can be viewed and/or any assailant can be identified and/or tracked.

In certain embodiments, the non-user electronic devices can include a drone aircraft (e.g., in the vicinity of the user. In this respect, when the drone aircraft receives an emergency signal from a user device, it can activate, take flight, and locate the user device and/or user. The drone aircraft can be equipped with any suitable imaging system and/or tracking system for locating, imaging, and or tracking the user in an emergency condition. This can provide authorities and/or other security personnel with enhanced information and tracking of users in an emergency condition. It is to be understood the data from various non-user devices, as illustratively discussed above, may be aggregated to be shared with other user devices 200 and/or with monitoring services to provide forensic monitoring and/or re-creation of the emergency situations. For instance, when other user device(s) 200 are approaching a location of a recent/ongoing incident, the approaching user(s) can be notified to be vigilant in said incident location and/or prepare to offer assistance to the distressed user.

In other embodiments, device 200 is configured to capture video and audio data via microphones and camera(s) provided on the device 200 or from surrounding link devices, which may be triggered upon either route initiation and/or the determination of an above described emergency situation. This captured data may then be used to determine events which transpired and may also be upload to monitoring organizations.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features. The foregoing description should therefore be considered as merely illustrative of the principles, teachings and exemplary embodiments of this invention, and not in limitation thereof.

It is to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A computer-implemented method for monitoring a condition of a user, said method comprising:
    receiving, at a mobile device, at least one signal from a condition sensor wherein the condition sensor is a sonic device configured to ping surroundings of the user to indicate movement of at least one object relative to the user; and
    determining if the received signal deviates from a threshold value.

2. The method of claim 1, further including the step of determining if a condition is an emergency condition relative to the user based on if the received signal deviates from the threshold value by a prescribed amount.

3. The method of claim 2, wherein the at least one object includes at least one of people, vehicles, or animals.

4. The method of claim 2, wherein the condition is determined to be an emergency condition if the location of the at least one object is within a predetermined personal space of the user.

5. The method of claim 1, wherein the mobile device is a mobile phone.

6. The method of claim 1, further comprising transmitting a signal to a monitoring body if an emergency condition is determined.

7. The method of claim 1, further comprising notifying the user if an emergency condition is determined.

8. The method of claim 7, wherein notifying the user includes activating a tactile, auditory, or other alarm to indicate an emergency condition to the user for the user to take emergency action.

9. The method of claim 1, further comprising transmitting an emergency signal to one or more non-user electronic devices within a monitoring network to notify the non-user electronic devices of an emergency condition.

10. The method of claim 1, wherein the non-user electronic devices include at least one of a camera, a mobile device of another person or officer in the vicinity, and/or an automated device configured to locate, follow, or otherwise monitor the user in the emergency condition.

11. A mobile computer device for monitoring a condition of a user, comprising:

a condition sensor configured to ping surroundings of the user with at least one signal to indicate movement of at least one object relative to the user and to receive the at least one signal; and determining if the received signal deviates from a threshold value.

12. The mobile device as recited in claim 11, wherein the condition sensor is a sonic device.

13. The mobile device as recited in claim 11, further configured to determine if a condition is an emergency condition relative to the user based on if the received signal deviates from the threshold value by a prescribed amount.

14. The mobile device as recited in claim 13, wherein the at least one object includes at least one of people, vehicles, or animals.

15. The mobile device as recited in claim 13, wherein the condition is determined to be an emergency condition if the location of the at least one object is within a predetermined personal space of the user.

16. The mobile device as recited in claim 11, wherein the mobile device is a mobile phone.

17. The mobile device as recited in claim 11, further configured to transmit a signal to a monitoring body if an emergency condition is determined.

18. The mobile device as recited in claim 17, further configured to notify the user if an emergency condition is determined.

19. The mobile device as recited in claim 18, wherein notifying the user includes activating a tactile, auditory, or other alarm to indicate an emergency condition to the user for the user to take emergency action.

20. The mobile device as recited in claim 11, further configured to transmit an emergency signal to one or more non-user electronic devices within a monitoring network to notify the non-user electronic devices of an emergency condition.

* * * * *